United States Patent [19]

Liess et al.

[11] Patent Number: 4,807,632

[45] Date of Patent: Feb. 28, 1989

[54] MEASURING INSTRUMENT FOR INTRACARDIAL ACQUISITION OF THE BLOOD OXYGEN SATURATION OF A PATIENT FOR CONTROLLING THE PACING RATE OF A HEART PACEMAKER

[75] Inventors: Hans D. Liess, Muensing; Roland Heinze, Munich, both of Fed. Rep. of Germany

[73] Assignee: Siemens Aktiengesellschaft, Berlin and Munich, Fed. Rep. of Germany

[21] Appl. No.: 52,032

[22] Filed: May 19, 1987

[30] Foreign Application Priority Data

May 22, 1986 [DE] Fed. Rep. of Germany ....... 3617180

[51] Int. Cl.$^4$ ........................................... G01D 18/00
[52] U.S. Cl. .............................. 128/634; 128/419 PT; 250/252.1; 356/41; 73/1 R
[58] Field of Search ................. 128/633, 634, 419 PT; 356/41; 250/252.1 A; 73/1 R

[56] References Cited

U.S. PATENT DOCUMENTS

| | | | |
|---|---|---|---|
| 4,399,820 | 8/1983 | Wirtzfeld et al. | 128/632 X |
| 4,407,290 | 10/1983 | Wilber | 356/41 X |
| 4,603,700 | 8/1986 | Nichols et al. | 128/633 |
| 4,700,708 | 10/1987 | New, Jr. et al. | 250/252.1 A |

FOREIGN PATENT DOCUMENTS 2717659 10/1978 Fed. Rep. of Germany.
3152963 9/1982 Fed. Rep. of Germany.

Primary Examiner—William E. Wayner

[57] ABSTRACT

A measuring instrument for the intracardial acquistion of the blood oxygen saturation of a patient for use in controlling a heart pacemaker implanted in the patient has a measuring probe with a measuring current path which includes a light transmitter and a light receiver which receives light emitted by the light transmitter and reflected by the blood. The measuring probe is connected to an evaluation circuit via two lines. A useful signal measurement and a reference measurement, independent of the blood reflection, are made and the blood oxygen saturation is identified by comparing the two signals. A separate evaluation of the useful signal measurement and the reference signal measurement is enabled by making the useful signal measurement chronologically offset with respect to the reference measurement in one embodiment, or by using the amplitude of the current from the light receiver to make one measurement, and using the voltage amplitude to make the other measurement in another embodiment.

19 Claims, 4 Drawing Sheets

MEASURING INSTRUMENT FOR INTRACARDIAL ACQUISITION OF THE BLOOD OXYGEN SATURATION OF A PATIENT FOR CONTROLLING THE PACING RATE OF A HEART PACEMAKER

BACKGROUND OF THE INVENTION

1. Field of the Invention

The present invention is directed to a measuring instrument for intracardial acquisition of the blood oxygen saturation of a patient, and in particular to such a measuring instrument for use in controlling the pacing rate of a heart pacemaker implanted in the patient.

2. Related Application

The subject matter of the present application is related to the subject matter of copending application Ser. No. 051,857 (Roland Heinze and Hakan Elmqvist) filed May 20, 1987.

3. Description of the Prior Art

German OS No. 31 52 963 discloses a measuring probe for generating a signal corresponding to the blood oxygen saturation of a patient including a measuring current path with a light transmitter and a light receiver arranged such that the light receiver receives light emitted by the light transmitter and reflected by the blood. This known device undertakes a useful signal measurement and a reference measurement independent of the blood reflection through the measuring probe. The measuring probe is connected to an evaluation circuit through two lines, the evaluation circuit charging the measuring probe with a current or with a voltage, and thereby permitting separate evaluation of the signals arising during useful signal measurement and reference signal measurement. The light emitter in this known device is a light emitting diode, and the light receiver is a phototransistor. The light emitting diode and the phototransistor are connected in parallel such that the conducting state current through the light emitting diode is superimposed with the current through the phototransistor caused by the incident light. If the measuring probe is driven with a constant current or with a constant voltage, the light reflected by the blood, dependent on the blood oxygen saturation thereof, triggers a current flow in the phototransistor which effects a current (or voltage) modification at the measuring probe. The voltage or current modification generated by the light reflection is identified in an evaluation circuit by comparing the measured signal, which is obtained when the light emitting diode and the phototransistor are driven, with a reference signal. The reference signal is formed by a pulse of the same operating voltage, but having an inverted operational sign in comparison to the voltage used for the useful signal measurement. This pulse is supplied through a diode connected with opposite plurality to the pularity of the light emitting diode. The operating characteristics of the diode in the reference circuit and the characteristics of the light emitting diode are preferably identical.

In this known measuring instrument, therefore, only two electrical leads are necessary for obtaining the useful signal measurement and the reference measurement. This is an advantage because such leads must be accomodated in a catheters having the smallest possible diameter and great flexibility, both of which are decreased by the presence of more electrical leads. Moreover, every additional electrical lead increases the probability of a failure.

A disadvantage of this known device, however, is that the voltage used for obtaining the measured signal must be reversed in polarity in order to make the reference measurement. Given the standard format for the voltage supply of heart pacemakers, wherein one pole of the supply voltage is rigidly connected to the housing, a substantial circuit outlay is required in order to make this polarity reversal. Additionally, the same current is used for the reference measurement as for the useful signal measurement.

Other commercially available devices are known wherein an infrared emitting diode is connected for making the reference measurement, with the receiver remaining in operation during the reference measurement as well. The wavelength of the infrared emitting diode is selected such that the reflection of the blood is independent of its oxygen saturation. A reference measurement is thereby obtained which permits deposits on the measuring probe to be taken into account.

SUMMARY OF THE INVENTION

It is an object of the present invention to provide a measuring instrument for the intracardial acquisition of the blood oxygen saturation of a patient for use in controlling the pacing rate of a heart pacemaker implanted in the patient wherein only two electrical leads are needed and wherein a reference measurement is made without the necessity of reversing the polarity of the voltage used to obtain the measured signal.

The above object is achieved in a first embodiment wherein a current or voltage of a selected polarity is supplied to the measuring probe, and wherein the supplied current is used chronologically offset in the measuring probe for making the useful signal measurement and for making the reference measurement. A useful signal measurement and a reference measurement independent thereof are thus possible without reversing the polarity of (repolarizing) the measuring voltage. Moreover, only one common measuring pulse for reference measurement and useful signal measurement is required. As a result, transient responses occur only once, and this common measuring pulse can be made shorter in duration than measuring pulses in conventional devices. A saving in current is thereby achieved.

The above object is achieved in a second embodiment wherein the reference measurement is made in the measuring probe for as long a time as the measuring probe is charged with a current or voltage below a limit value, and a useful signal measurement is made in the measuring probe as soon as the current or voltage exceeds this limit value. A separation of the useful signal measurement and the reference measurement without changing the polarity of the current or voltage is thus possible because these two measurement are made with different currents. An advantage of this embodiment is that a lower current is required for the reference measurement than for the useful signal measurement, again resulting in a current saving.

In one embodiment, the measured current path contains a series circuit including a resistor and a light-sensitive diode, with a transistor being connected in parallel with this series circuit. The base of the transistor is connected to the junction of the resistor and the light-sensitive diode. The capacitance of the light-sensitive diode is sufficient to delay turning on of the transistor, and thus of the measuring current circuit.

In a further embodiment, a switching means driven by a time delay element connects an infrared-emitting diode to the input terminals of the measuring probe before expiration of the delay time, and connects the infrared-emitting diode to the input terminals of the measuring probe after expiration of the delay time. The time delay element responds to the application of a voltage or a current to the measuring probe, so that the measuring current path remains switched on in both positions of the switching means. The reference measurement using the infrared-emitting diode can thus be made in a simple way.

In a circuit realizing this embodiment, a first switch is connected in series with a reference current path which is activated during the reference measurement, and a second switch is in series with the measuring series path. The first switch is closed and the second switch is opened when the measuring probe is charged with a low current, and the second switch is closed when the measuring probe is charged with a higher current. An evaluation circuit charges the measuring probe with a low current for reference measurement and charges the measuring probe with a higher current of the same polarity for useful signal measurement.

In the embodiment wherein an infrared-emitting diode is used for making the reference measurement, the measuring probe can include the parallel circuit of an infrared-emitting diode, a conventional light-emitting diode, and a measuring current path, with a first switch connected in series with the infrared-emitting diode and a second switch connected in series with the light-emitting diode. The first switch is closed and the second switch is opened when the measuring probe is charged with a low current, and the second switch is closed when the measuring probe is charged with a higher current. An evaluation circuit again charges the measuring probe with a low current for reference measurement, and charges the measuring probe with a higher current of the same polarity for useful signal measurement.

A bipolar EKG signal measurement can be made by disposing the measuring probe in a bipolar lead in an electrode arrangement having a stimulation (active) electrode and a passive electrode, such that the electrode arrangement is in parallel with the measuring probe. A switch is disposed in the connecting line to one of the two electrodes, this switch being opened as soon as the measuring probe is charged with voltage by the evaluation circuit. The switch may be an n-channel field effect transistor having a source-drain path in the lead to the passive electrode, and having a gate controlled by a threshold switch which monitors the voltage at the measuring probe.

As used herein, the term "applied signal" refers to the signal which is applied to the measuring probe by the evaluation circuit. In the first embodiment described above, this applied signal may be either a voltage pulse or a current pulse. In the second embodiment, the applied signal may be a continuously rising voltage or current. All embodiment have in common, however, the use of a single applied signal to make both a reference measurement and a useful signal measurement, the use of only two leads connected to the measuring probe, and the avoidance of a polarity reversal of the applied signal during the measuring process.

DESCRIPTION OF THE PREFERRED EMBODIMENTS

Figure 1:
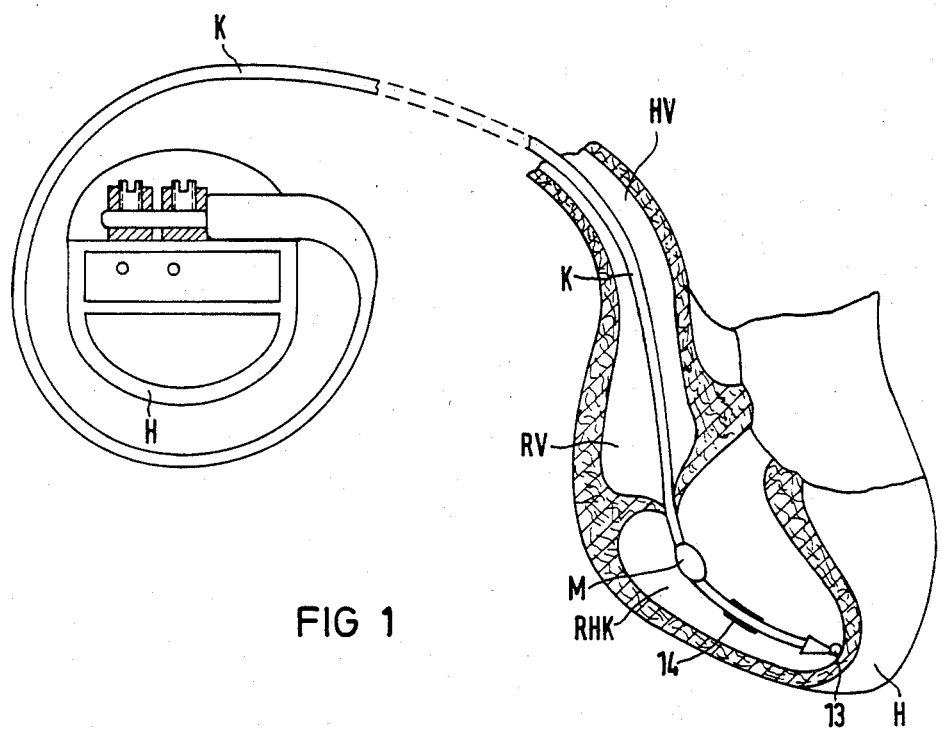
FIG. 1 is a schematic showing of the manner of arranging a measuring probe, connected to a heart pacemaker, in the heart of a patient.

As shown in FIG. 1, a heart pacemaker H has a catheter K containing two electrical leads which is introduced into the superior vena cava HV and extends through the right atrium RV and into the right ventrical RHK of a heart H. A measuring probe M for measuring the blood oxygen saturation of the patient is disposed within the right heart ventricle RHK. The heart muscle is excited by a stimulation electrode 14. A passive electrode 13 is also provided.

Figure 2:
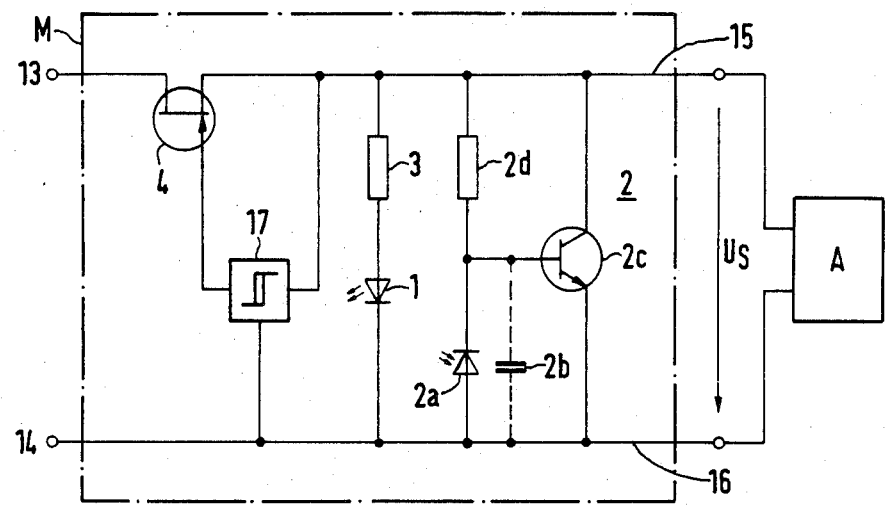
FIG. 2 is a circuit diagram of a first embodiment of a measuring instrument constructed in accordance with the principles of the present invention.

A first embodiment of circuitry for the measuring probe M is shown in FIG. 2. In this embodiment, a series circuit consisting of a light-emitting diode 1 operating as a light transmitter and a resistor 3, the series circuit of a resistor 2d and a light-sensitive diode 2a operating as a light receiver, and a transistor 2c are connected in parallel to the leads from the electrodes 13 and 14. The conducting directions of the light emitting diode 1 and the light-sensitive 2a are opposite. The junction of the resistor 2d and the light sensitive diode 2a is connected to the base of the transistor 2c.

Figure 3:
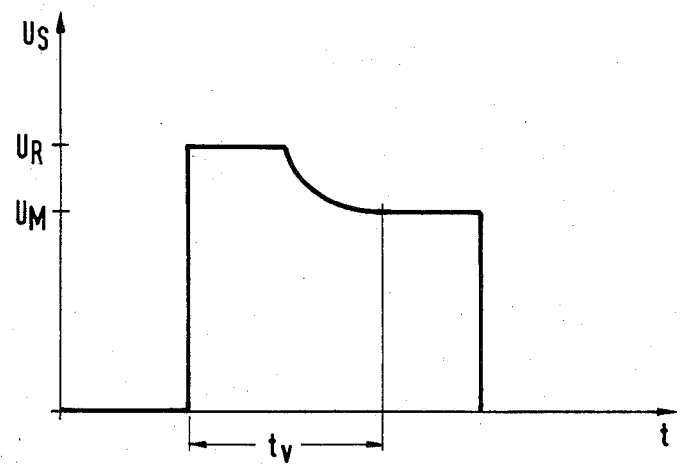
FIG. 3 is a voltage/time diagram for explaining the operation of the circuit shown in FIG. 2.

When the measuring probe M is charged with a voltage or current pulse by an evaluation circuit A disposed in the heart pacemaker H, current initially flows only through the series circuit consisting of the resistor 3 and the light emitting diode 1, which serves as a reference current path. A resulting test voltage $U_R$ thus depends only on the resistance of the light-emitting diode 1, the resistor 3, and the lead resistances. The transistor 2c is still inhibited, because a capacitor 2b has not yet been charged. The capacitor 2b may be simply formed by the internal capacitance of the light-sensitive diode 2a, and is therefore shown connected by dashed lines. Following a delay time $t_v$, the capacitor 2b is charged through the resistor 2d, and only then does the transistor 2c become conducting so that the measuring probe M is charged with an impressed current. This defines the measuring voltage $U_M$, as shown in FIG. 3.

The conductivity of the transistor 2c is dependent on the conductivity of the light-sensitive diode 2a. The light-sensitive diode 2a is arranged so as to receive light emitted by the light-emitting diode 1 and reflected by the blood dependent on the oxygen saturation of the blood. The test or measuring voltage $U_M$ thus represents a measure of the oxygen saturation of the blood.

The test voltage $U_M$, however, is also dependent on the resistance of the connecting lines and on the temperature of the measuring probe M. These sources of error, however, can be compensated by the use of the previously identified reference voltage $U_R$, which also contains these errors. For this purpose, the difference $\Delta U_F = U_R - U_M$ is used, this difference $\Delta U_F$ representing the actual measured signal which can be analyzed in the manner described, for example, in the aforementioned German OS No. 31 52 963.

In an analogous manner, the measuring probe M can alternatively be charged with an impressed voltage, in which case the current is then used as the measured quantity.

In the embodiment of FIG. 2, a field effect transistor 4 is connected to the lead 15 from the passive electrode 13. The gate of this field effect transistor 4 is connected to a threshold circuit 17, which monitors the voltage at the measuring probe M. As soon as the evaluation circuit A charges the measuring probe M with a voltage, the field effect transistor 4 is inhibited, so that the passive electrode 13 is essentially disconnected from the lead 15. This results in the following advantage.

A two electrode arrangement, such as a passive electrode 13 and stimulation electrode 14, is preferable for obtaining an EKG signal from the heart which is free of disturbances. If, however, the passive electrode 13 were not disconnected during a measuring procedure using the measuring probe M, the voltage charging of the measuring probe M by the evaluation circuit A would always result in an undesired stimulation pulse to the heart. This is avoided in the circuit of FIG. 2 because the passive electrode 13 is disconnected from the measuring probe M during voltage charging thereof. Also avoided are measuring errors caused by the resistance between the passive electrode 13 and the stimulation electrode 14 formed by body tissue.

A disruption of the EKG measurement by the measuring probe M does not occur because the EKG voltages are below the threshold voltages of the measuring probe circuit.

Figure 4:
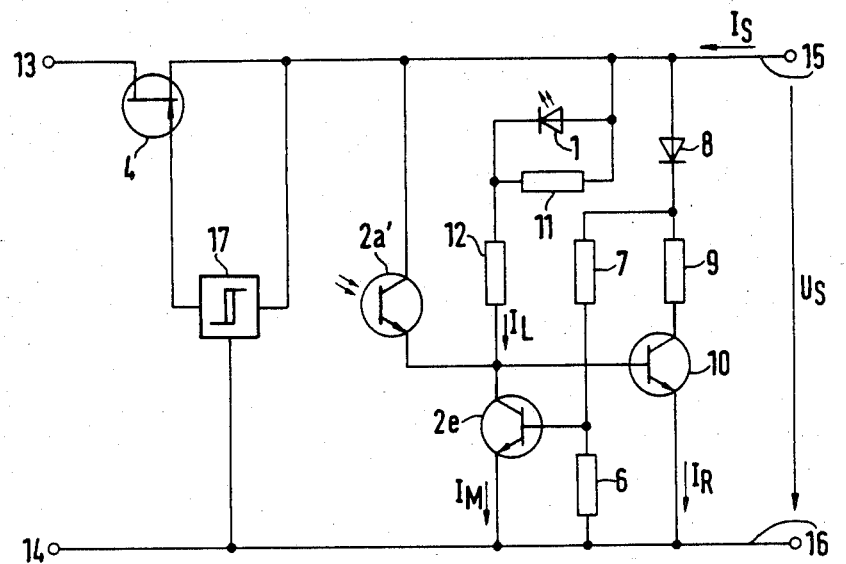
FIG. 4 is a circuit diagram of a second embodiment of a measuring instrument constructed in accordance with the principles of the present invention.
Figure 5:
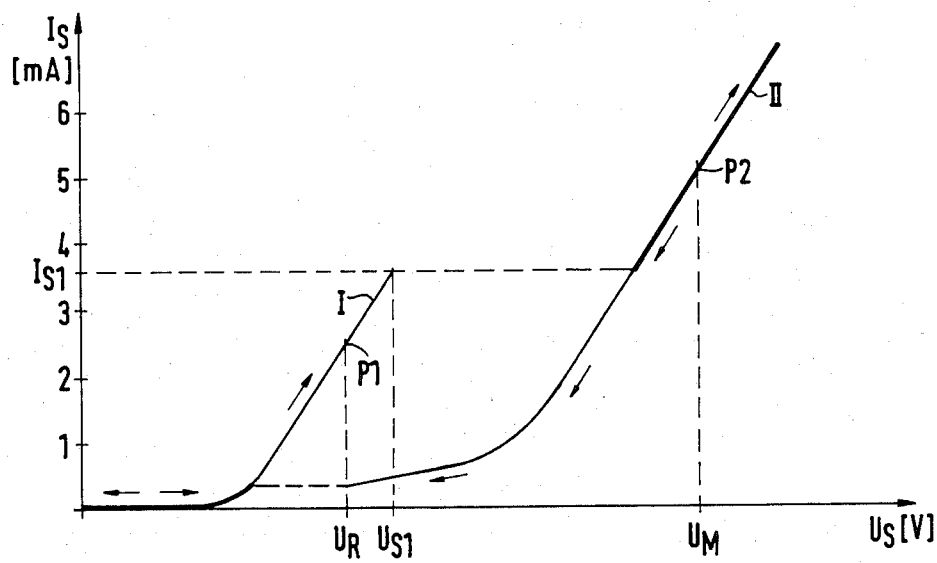
FIG. 5 is a current/voltage diagram for explaining the operation of the circuit of FIG. 4.

An alternative embodiment operating in accordance with the principles of the present invention is shown in FIG. 4. For this embodiment, the dependency of the current $I_S$ in the measuring probe M on the applied voltage $U_S$ is shown in FIG. 5. A series connection of a diode 8, a resistor 9, and a transistor 10 is connected between the leads 15 and 16. A light-emitting diode 1 with a resistor 11 connected in parallel therewith, a resistor 12, and the collector-emitter path of a transistor 2e are connected in series across the leads 15 and 16. A phototransistor 2a' is connected between the lead 15 and the junction of the resistor 12 and the transistor 2e. This junction is also connected to the base of the transistor 10. A voltage divider consisting of resistors 6 and 7 is connected between the junction of the diode 8 and the resistor 9, and the lead 16. The tap of this voltage divider is connected to the base of the transistor 2e.

When the current $I_S$ flowing through the connecting lines 15 and 16 rises, the transistor 10 becomes conducting through the resistors 11 and 12, while the transistor 2e is still non-conducting. The current path through the diode 8, the resistor 9 and the transistor 10 therefore determines the voltage at the measuring probe M. This portion of the current/voltage curve is referenced I in FIG. 5. The current path consisting of the diode 8, the resistor 9 and the transistor 10 serves as a reference current path, with the reference measurement being made, for example, at an operating point references P1 in FIG. 5. The resistance of the leads and the temperature of the measuring probe is first acquired with this reference measurement.

When the voltage $U_S$ at the measuring probe continues to increase, the transistor 2e is switched to a conducting state via the voltage divider comprising the resistors 6 and 7. The voltage value $U_{S1}$ or the current value $I_{S1}$ resulting therefrom is defined by the division ratio of the resistors 6 and 7 and by the value of the resistance of the resistor 9. As soon as the transistor 2e is switched on, the transistor 10 becomes inhibited because its base-emitter voltage is shorted. The current $I_S$ supplied to the measuring probe is thus switched from the reference current path to the measuring current path consisting of the light-emitting diode 1 and the phototransistor 2a'. This portion of the current/voltage curve is referenced II in FIG. 5. The current exhibits a hysteresis, i.e., switching back to the reference circuit is not undertaken even though the current $I_S$ decreases, until significantly lower values occur than those which occurred given a rising current, as can be seen in FIG. 5.

After switching to the measuring circuit, the measuring current or measuring voltage can again be acquired, because the conductivity of the phototransistor 2a' is dependent on the portion of the light from the light-emitting diode 1 which is reflected by the blood oxygen. For example, measurement may be made around an operating point referenced P2 in FIG. 5. As in the case of the previous embodiment, the preceding reference measurement is used in the evaluation circuit for correction of the influences of temperature and lead resistance.

As in the embodiment of FIG. 2, a field effect transistor 4 can be connected in the lead 15 to the passive electrode 13 as a switch for disconnecting the passive electrode 13 during the measuring procedure. As in the embodiment of FIG. 2, the control electrode (gate) of the transistor 4 is connected to the threshold circuit 17.

Figure 6:
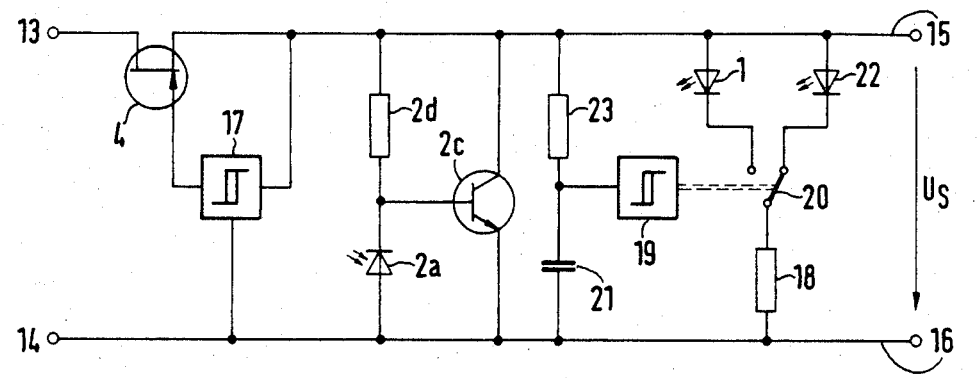
FIG. 6 is a circuit diagram of a further embodiment of a measuring instrument constructed in accordance with the principles of the present invention.

A further embodiment is shown in FIG. 6 wherein a reference measurement is made using an infrared emitting diode 22. A light emitting diode 1 or the infrared emitting diode 22 are optionally connectable across the leads 15 and 16 through a resistor 18 and a switch 20.

An RC element comprising a capacitor 21 and a resistor 23 is series is also connected across the leads 15 and 16, with the capacitor 21 being connected to the lead 16. A threshold switch 19, which controls the switch 20, is connected to the tap of the RC element. A measuring circuit is also connected between the leads 15 and 16 consisting of a transistor 2c and the series connection of a resistor 2d and a light-sensitive diode 2a, the resistor 2d and the diode 2a being connected in parallel to the transistor 2c. The base of the transistor 2c is connected to the junction of the resistor 2d and the light sensitive diode 2a. A threshold switch 17 connected to the gate of a field effect transistor 4 is also provided in the embodiment of FIG. 6, functioning as in the previously-described embodiments.

When the measuring probe M is charged with a current or voltage pulse, the switch 20 initially is connected in the position shown in FIG. 6, so that the infrared emitting diode 22 is energized, and the emitted infrared radiation is received by the light-sensitive diode 2a. The transistor 2c is thereby driven in accord with the conductivity of the diode 2a.

The wavelength of the infrared radiation is selected such that the reflection thereof is independent of the blood oxygen saturation. A reference signal is thus obtained which includes factors corresponding to the lead resistance, the temperature of the device, and reflections caused by possible deposits on the measuring probe.

Additionally, a timing element consisting of the RC element (resistor 23 and capacitor 21) and the threshold element 19 is also set simultaneously with the charging of the measuring probe M with a current or voltage pulse. This timing element causes the switch 20 to switch position after the expiration of a prescribed delay time. The light emitting diode 1 thus becomes energized, and its reflected light is received by the light-sensitive diode 2a.

In all of the embodiments discussed above, the light emitted by the light-emitting diode 1 has a wavelength at which reflection thereof is dependent on the blood oxygen saturation, so that a useful signal measurement can be undertaken. By comparison with the reference measurement, the aforementioned sources of error (lead resistance, temperature of the device and reflection due to deposits) can be eliminated.

Figure 7:
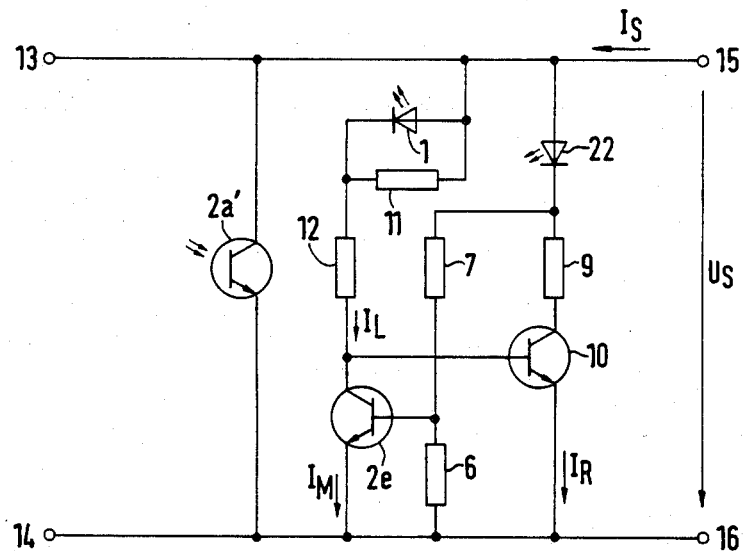
FIG. 7 is a circuit diagram of another embodiment of a measuring instrument constructed in accordance with the principles of the present invention.

Another embodiment constructed in accordance with the principles of the present invention is shown in FIG. 7 wherein, similar to the embodiment of FIG. 4, a reference measurement and useful signal measurement can be discriminated by the height of the applied voltage or current. In comparison to the embodiment of FIG. 4, the diode 8 is replaced in the embodiment of FIG. 7 by an infrared diode 22. Furthermore, in FIG. 7, the phototransistor 2a' receiving the reflected light is directly connected between the leads 15 and 16.

Switching from the infrared emitting diode 22 operated during reference measurement to the light-emitting diode 1 operated during the useful signal measurement is made in the manner already described in connection with FIG. 4.

In contrast to the embodiment of FIG. 4, however, the light emitted by the infrared-emitting diode 22 and received by the phototransistor 2a' is also received in the embodiment of FIG. 7 during the reference measurement. This is for the purpose, as in the embodiment of FIG. 6, to additionally take into account reflections due to deposits on the measuring probe M in the reference measurement.

Although modifications and changes may be suggested by those skilled in the art it is the intention of the inventors to embody within the patent warranted hereon all changes and modifications as reasonably and properly come within the scope of their contribution to the art.

We claim as our invention:

1. An instrument for intracardial acquisition of blood oxygen saturation in a sequence including making a reference measurement and a useful signal measurement, said instrument comprising:
   a measuring probe having two leads, a light transmitter, means for generating said useful signal connected between said leads including a measuring current path having said light receiver therein, said light transmitter and light receiver disposed such that said light receiver receives light from said light transmitter reflected by the blood dependent on the degree of oxygen saturation of said blood;
   an evaluation circuit connected to said measuring probe leads, said evaluation circuit supplying one applied signal for each sequence, said applied signal having non-changing polarity and being used for enabling both said reference measurement and said useful signal measurement; and
   means for separately generating said reference signal and said useful signal in sequence in response to said applied signal.

2. An instrument as claimed in claim 1, wherein said applied signal is a pulse.

3. An instrument as claimed in claim 2, wherein said light receiver is a light-sensitive diode having a capacitance, and wherein said measuring current path consists of said light-sensitive diode and a resistor connected in series therewith, and wherein said means for separately generating said reference signal and said useful signal is a transistor having a collector-emitter path connected across said leads and a base connected between said resistor and said light-sensitive diode, whereby said transistor is non-conducting at a beginning of said pulse during which said reference signal is generated, and said transistor becomes conducting when the charge developed by said capacitance due to the degree of conduction of said light-sensitive diode resulting from light incident thereon from said light transmitter reaches a level sufficient to turn on said transistor at which time said useful signal is generated.

4. An instrument as claimed in claim 3, further comprising a reference current path in parallel with said measuring current path across said leads, said reference current path consisting of said light transmitter and a resistor connected in series therewith.

5. An instrument as claimed in claim 3, further comprising a reference current path in parallel across said leads with said measuring current path, said reference current path consisting of an infrared emitting diode connected in series with a switch and a resistor, said light transmitter being also connectable to said switch, and said instrument further comprising a time delay means for operating said switch to energize said infrared emitting diode at a beginning of said pulse during said reference measurement and to switch said switch after a delay to energize said light transmitter during said useful signal measurement.

6. An instrument as claimed in claim 5, wherein said time delay means comprises:
   a capacitor connected in series with a resistor between said leads; and
   a threshold circuit having an input connected to the junction of said capacitor and said resistor, said threshold circuit having a threshold voltage associated therewith,
whereby said capacitor is charged during generation of said reference signal and said threshold circuit switches said switch upon the voltage across said capacitor attaining said threshold voltage.

7. A measuring instrument as claimed in claim 1, wherein said applied signal is a continuously rising signal.

8. A measuring instrument as claimed in claim 7, further comprising a first switch in said measuring current path and a second switch connected in series with said light transmitter forming a reference current path therewith between said leads, said first and second switches being respectively responsive to said applied signal such that said applied signal initially closes said first switch and opens said second switch for generation of said reference signal and subsequently as said applied signal continues rising said second switch is closed and said first switch is opened for generating said useful signal.

9. A measuring instrument as claimed in claim 8, further comprising a voltage divider connected in parallel with said first switch, and wherein said second switch is a transistor having a base electrode connected to a tap of said voltage divider.

10. An instrument as claimed in claim 8, wherein said first switch is a transistor having a control electrode connected to a junction between said light transmitter and said second switch.

11. An instrument as claimed in claim 8, further comprising an infrared-emitting diode connected in parallel with said light emitting diode between one of said leads and said second switch, whereby said infrared emitting diode is energized during generation of said reference signal and said light-emitting diode is energized during generation of said useful signal.

12. An instrument as claimed in claim 1, for use with a heart pacemaker, and wherein said two leads simultaneously serve as leads for two electrodes of said pacemaker, said measuring probe being connected to said leads between said pacemaker and said electrodes, and said instrument further comprising means for momentarily disconnecting one of said leads from one of said electrodes so that said applied signal is not transmitted to the heart.

13. An instrument as claimed in claim 12, wherein said means for disconnecting comprises:
a threshold circuit connected between said leads and having a threshold voltage associated therewith; and
a switch having a conducting path in series with one of said leads and a control electrode connected to an output of said threshold circuit,
whereby said threshold circuit, upon said applied signal exceeding said threshold voltage, supplies a signal to said control electrode of said switch to open said switch and thereby disconnect said electrode.

14. An instrument as claimed in claim 13, wherein said switch is an n-channel field effect transistor having a source-drain path connected in series with said one of said leads, and a gate electrode which is said control electrode connected to said threshold circuit.

15. An instrument for intracardial acquisition of blood oxygen saturation using a measuring probe having two leads in a sequence including making a reference signal measurement and a useful signal measurement, said instrument comprising:
a light transmitter connected in said measuring probe between said leads;
a measuring current path in said measuring probe connected between said leads including a light-sensitive diode and a resistor connected in series therewith;
a normally open switch having a conducting path connected between said leads and a control terminal connected to a junction between said light-sensitive diode and said resistor;
a capacitor connected in parallel with said light-sensitive diode between said junction and one of said leads; and
an evaluation circuit connected to said leads which supplies a pulse to said measuring probe for each sequence and which measures the voltage across said leads,
whereby said pulse initially energizes said light transmitter with said normally open switch being non-conducting for making said reference signal measurement and charging said capacitance by the action of said light from said transmitter on said light sensitive diode reflected by the blood oxygen, said normally open switch closing upon attainment of said selected charge on said capacitance for making said useful signal measurement.

16. An instrument as claimed in claim 15, wherein said capacitance is the internal capacitance of said light-sensitive diode.

17. An instrument as claimed in claim 15, further comprising:
a further switch connected in series with said light transmitter between said leads;
an infrared emitting diode connected in parallel with said light transmitter between said further switch and one of said leads, said further switch normally completing a path between said leads including said infrared emitting diode, and said switch having a control terminal; and
a time delay means connected to said control terminal for operating said switch,
whereby said infrared emitting diode is initially energized at a beginning of said pulse for use in making said reference signal measurement, said time delay means thereafter changing said switch to complete a conducting path between said leads including said light transmitter for making said useful signal measurement.

18. An instrument for intracardial acquisition of blood oxygen saturation using a measuring probe having two leads in a sequence including making a reference signal measurement and a useful signal measurement, said instrument comprising:
a first switch having a conducting path connected between said leads and a control electrode connected to one of said leads;
a light transmitter connected in series with a conducting path of a second switch between said leads, said second switch having a control electrode;
a voltage divider connected in parallel with said conducting path of said first switch and having a tap connected to said control electrode of said second switch;
a light receiver connected between said leads, said light receiver disposed for receiving light from said light transmitter reflected by said blood oxygen and generating a current proportional thereto; and
an evaluation circuit connected to said leads which supplies a continuously rising signal to said measuring probe and which measures the voltage across said leads,
whereby said first and second switches are respectively responsive to said continuously rising signal such that said first switch is initially closed and said second switch is initially open during said reference signal measurement, and said first switch is thereafter opened and said second switch is thereafter closed for making said useful signal measurement.

19. An instrument as claimed in claim 18, further comprising an infrared emitting diode connected in series with said conducting path of said first switch between said leads, such that said reference signal measurement is made with said infrared emitting diode energized and said useful signal measurement is made with said light transmitter energized.

* * * * *